United States Patent
Byeon et al.

(10) Patent No.: US 12,180,237 B2
(45) Date of Patent: Dec. 31, 2024

(54) METHOD FOR PREPARING GADOBUTROL

(71) Applicant: ST PHARM CO., LTD., Siheung-si (KR)

(72) Inventors: Changho Byeon, Ansan-si (KR); Hoejin Yoon, Ansan-si (KR); Moonsu Kim, Ansan-si (KR); Seongsu Jeong, Ansan-si (KR); Jongmoon Park, Siheung-si (KR); Junwon Lee, Anyang-si (KR); Seokhun Woo, Yongin-si (KR); Sun Ki Chang, Gunpo-si (KR)

(73) Assignee: ST PHARM CO., LTD., Gyeonggi-do (KR)

( * ) Notice: Subject to any disclaimer, the term of this patent is extended or adjusted under 35 U.S.C. 154(b) by 985 days.

(21) Appl. No.: 17/270,268

(22) PCT Filed: Aug. 23, 2019

(86) PCT No.: PCT/KR2019/010802
§ 371 (c)(1),
(2) Date: Feb. 22, 2021

(87) PCT Pub. No.: WO2020/040617
PCT Pub. Date: Feb. 27, 2020

(65) Prior Publication Data
US 2021/0317142 A1    Oct. 14, 2021

(30) Foreign Application Priority Data

Aug. 23, 2018 (KR) .................. 10-2018-0098501

(51) Int. Cl.
*C07F 5/00* (2006.01)
(52) U.S. Cl.
CPC .......... *C07F 5/003* (2013.01); *C07B 2200/13* (2013.01)
(58) Field of Classification Search
CPC .... C07F 5/003; C07B 2200/13; C07D 257/02
USPC ................................. 534/7, 10–16
See application file for complete search history.

(56) References Cited

U.S. PATENT DOCUMENTS

| 9,822,084 B2* | 11/2017 | Lim | C07D 257/02 |
| 10,065,933 B2* | 9/2018 | Lim | C07F 5/003 |
| 10,072,027 B2* | 9/2018 | Platzek | C07D 257/02 |
| 10,435,417 B2* | 10/2019 | Platzek | A61K 49/106 |
| 2013/0116429 A1 | 5/2013 | Platzek | |
| 2016/0287726 A1 | 10/2016 | Tsourkas et al. | |
| 2016/0331849 A1 | 11/2016 | Kim et al. | |
| 2017/0106103 A1 | 4/2017 | Preihs et al. | |
| 2017/0260148 A1 | 9/2017 | Lim et al. | |

FOREIGN PATENT DOCUMENTS

| CN | 102933562 A | 2/2013 | |
| CN | 103613557 | 3/2014 | |
| CN | 105037288 A | 11/2015 | |
| CN | 106543094 A | 3/2017 | |
| CN | 107001294 A | 8/2017 | |
| CN | 108047151 A | 5/2018 | |
| CN | 108299322 A | 7/2018 | |
| EP | 0448191 A1 | 9/1991 | |
| KR | 10-2013-0089229 | 8/2013 | |
| KR | 10-2014-0035911 | 3/2014 | |
| KR | 10-2015-0083721 | 7/2015 | |
| KR | 10-2016-0032872 | 3/2016 | |
| KR | 10-2016-0079460 | 7/2016 | |
| KR | 10-1653064 | 9/2016 | |
| WO | 2012/143355 | 10/2012 | |
| WO | 2016/105172 | 6/2016 | |
| WO | WO-2016105172 A2 * | 6/2016 | ............. A61K 49/04 |
| WO | 2020154892 A1 | 8/2020 | |

OTHER PUBLICATIONS

Chinese Office Action and English Translation for corresponding Chinese Application No. 2019800551202, mailed Mar. 24, 2023, 16 pages.
Extended European Search Report for corresponding European Application No. 19851560.3, mailed Feb. 10, 2022, 7 pages.
Japanese Office Action and English Translation for corresponding Japanese Application No. 2021-506263, mailed Mar. 8, 2022, 9 pages.
International Search Report for PCT/KR2019/010802 mailed Dec. 2, 2019, 6 pages w/ English Translation.
Office Action for KR10-2018-0098501 dated Feb. 10, 2020, 10 pages w/ English Translation.
Notice of Allowance for KR10-2018-0098501 dated Jul. 27, 2020, 8 pages w/ English Translation.
Platzek et al., "Synthesis and Structure of a New Macrocyclic Polyhydroxylated Gadolinium Chelate Used as a Contrast Agent for Magnetic Resonance Imaging", Inorg. Chem. 1997, vol. 36, pp. 6086-6093.

* cited by examiner

*Primary Examiner* — Jake M Vu
(74) *Attorney, Agent, or Firm* — NIXON & VANDERHYE, PC

(57) ABSTRACT

The present invention provides a novel method for preparing high-purity gadobutrol or hydrates thereof. The preparation method of the present invention can have an advantage of simplifying a process by forming a gadolinium complex in-situ without purification of a butrol intermediate and omitting a resin purification process unlike a conventional method for synthesizing gadobutrol. In addition, the preparation method of the present invention can be used to produce high-purity gadobutrol or hydrates thereof at a high yield only through the simple process as above, and thus can be useful in mass production.

30 Claims, No Drawings

METHOD FOR PREPARING GADOBUTROL

CROSS-REFERENCE TO RELATED APPLICATION

This application is the U.S. national phase of International Application No. PCT/KR2019/010802 filed Aug. 23, 2019 which designated the U.S. and claims priority to Korean Patent Application No. 10-2018-0098501 filed on Aug. 23, 2018 with the Korean Intellectual Property Office, the entire contents of each of which are hereby incorporated by reference.

The present invention relates to a method for preparing gadobutrol and hydrates thereof. Specifically, the present invention relates to a method for preparing gadobutrol at a high yield rate by managing the purity of an intermediate thereof with high standards unlike a conventional synthesis method, as well as at a less cost through a simplified synthesis step thereof.

BACKGROUND OF THE INVENTION

In the field of gadolinium-containing contrast agents, gadobutrol has been released on the market worldwide under the trade name of Gadovist or Gadavist.

Gadobutrol represented by a following formula 1 is a racemate and a non-ionic complex of microcyclic ligand 10-(2,3-dihydroxy-1-(hydroxymethyl)propyl)-1,4,7,10-tetraazacyclodecane-1,4,7-triacetic acid (butrol) and gadolinium (III), which leads to a decrease in the relaxation time of protons in tissue water, especially at clinically recommended doses.

[Formula 1]

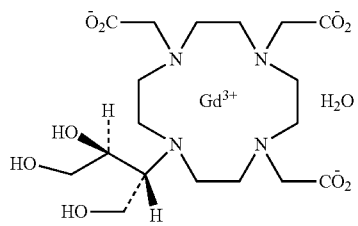

The method for synthesizing gadobutrol is particularly described in three paths (Schemes 1 to 3) in Inorg. Chem. 1997, 36, 6086-6093. However, in the above document, the path of Scheme 3 is unsuitable in terms of mass production due to its low yield, and produces gadobutrol having purity of about 90% when measured through HPLC (stationary phase: Hypersil phenyl (5 μm) of SHANDON; mobile phase: acetonitrile/borate buffer (pH 8) (volume ratio of 20/100); detection: UV detector (200 nm); injection volume: 10 μl).

In contrast, Scheme 1 has a disadvantage in that a large amount of resin is used for purification, and special facilities such as towers, etc., are required accordingly. Thus, the method of Scheme 1 is difficult to apply to mass production due to a rise in costs. In addition, Scheme 2 has a problem of having a low yield and a poor purity.

International standards such as ICH guidelines, etc., recommend that the content of impurities be 0.1% or less, and thus it is preferable that gadobutrol be prepared with an ultra-high purity of 99.9% or more in order to be released on the market as a drug. However, the methods disclosed in the above document are involved in a complicated process and cannot produce high-purity gadobutrol.

Thus, there has been a need to develop a novel method for preparing high-purity gadobutrol at a high yield rate, which is thus advantageous in terms of mass production, through a simple preparation process without a complicated purification process.

RELATED ART REFERENCE

Patent Document

Korean Registered Patent Publication No. 10-1653064

Non-Patent Document

Inorg. Chem. 1997, 36, 6086-6093

DETAILED DESCRIPTION OF THE INVENTION

Technical Problem

An object of the present invention is to provide a method for preparing high-purity gadobutrol or hydrates thereof at a high yield and at a low cost by managing the purity of an intermediate thereof with high standards only through a simple and smooth process.

Technical Solution

To achieve an object of the present invention, the present invention may provide a novel method for preparing gadobutrol or hydrates thereof.

Specifically, the preparation method of the present invention may include the following steps:

(S-1) subjecting a compound of formula 3 below or a salt thereof to a carboxymethylation reaction to prepare a compound of formula 2 below; and (S-2) subjecting the compound of said formula 2 to basic hydrolysis and forming a gadolinium complex in-situ to prepare a compound of formula 1 below:

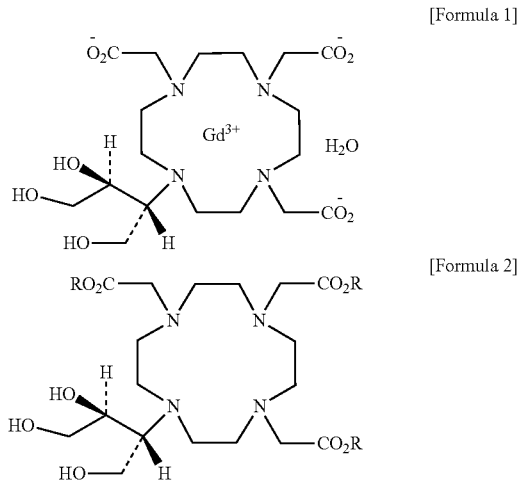

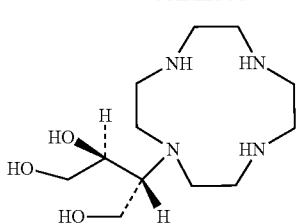

in the above formulas,

R is $C_1$-$C_4$ linear or branched-chain alkyl.

Hereinafter, the method will be described in detail for each step.

In the present specification, the term "hydrate" may refer to one in which an active ingredient and water are bonded to each other by a non-covalent intermolecular force, and may include a stoichiometric or non-stoichiometric amount of water. The hydrate may contain water at a ratio of about 0.25 to about 10 mol based on 1 mol of the active ingredient, and preferably may be a monohydrate containing 1 mol of water, but is not limited thereto.

In the present specification, the term "salt" may refer to a compound produced by a neutralization reaction between acid and base. In the present invention, the salt may include a salt that can be prepared by a conventional method, and may refer to an acid addition salt formed by free acid. For example, the types of salt of the present invention may include inorganic ion salts prepared from calcium, potassium, sodium, magnesium or the like; inorganic acid salts prepared from hydrochloric acid, nitric acid, phosphoric acid, bromic acid, iodic acid, perchloric acid, sulfuric acid or the like; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbric acid, carbonic acid, vanillic acid or the like; sulfonic acid salts prepared from methanesulfonic acid, ethanesulfonic acid, benzenesulfonic acid, salicylic acid, p-toluenesulfonic acid, naphthalenesulfonic acid or the like; amino acid salts prepared from glycine, arginine, lysine, etc.; amine salts prepared from trimethylamine, triethylamine, ammonia, pyridine, picoline, etc.; or the like, but are not limited thereto.

In the present specification, the term "carboxymethylation" may mean that an intrinsic bond is formed between a substrate and a carboxymethyl group.

In the present specification, the term "basic hydrolysis" may refer to hydrolysis performed in the presence of base, which is a decomposition reaction caused by the action of water molecules during a chemical reaction in nature. In the present invention, the above term may refer to a saponification reaction, which is a basic hydrolysis reaction of ester.

In the present specification, the term "in-situ" may mean that reactions occur in one container. In general, it is said to be reacted in-situ when two or more processes are continuously performed in one chamber. The present invention relates to an invention in which a gadolinium complex is formed in situ after a basic hydrolysis reaction occurs.

In the present specification, the term "complex" may mean that several other atoms, ions, molecules, atomic groups or the like are three-dimensionally coordinated with a direction around one or more atoms or ions so as to form one atomic group. In particular, a complex in which a central atom is a metal or a similar metal element may refer to a metal complex. The present invention relates to a method for preparing a metal complex compound represented by formula 1 in which the central atom is gadolinium.

In the present specification, the term "$C_x$-$C_y$" may refer to a functional group having x or more and y or less carbon atoms.

Step (S-1): Carboxymethylation Reaction

In the preparation method of the present invention, the step (S-1) relates to a carboxymethylation reaction in which a compound of formula 2 below is prepared by using a compound of formula 3 below or a salt thereof as a starting material.

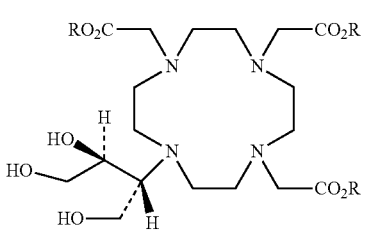

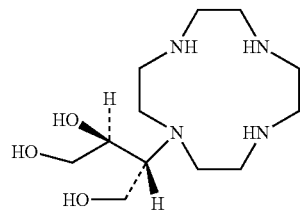

R is as defined above.

According to a specific embodiment of the present invention, in the step (S-1), the compound of said formula 2 may be prepared by reacting the compound of said formula 3 or the salt thereof with a compound of formula 4 below in the presence of base:

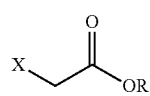

in above formula 4,

R is as defined above, and

X is halogen, TsO⁻ or MsO⁻.

In the present specification, the term "halogen" may represent Group 17 elements of the periodic table and may include, for example, fluorine (F), chlorine (Cl), bromine (Br) or iodine (I).

In the present specification, the term "TsO⁻" may be referred to as tosylate, and may be represented by an anion ($CH_3C_6H_4SO_3^-$) of p-toluene sulfonic acid. Tosylate may be abbreviated as TsO⁻ as above or may be called an ester of p-toluene sulfonic acid, and may be used as a good leaving group in organic reactions.

In the present specification, the term "MsO⁻" may be referred to as mesylate, and may be represented by an anion ($CH_3SO_3^-$) of methane sulfonic acid ($CH_3SO_3H$). Mesylate may be abbreviated as MsO⁻ as above or may be called an ester of methane sulfonic acid, and may be used as a good leaving group in organic reactions.

According to a specific embodiment of the present invention, the salt of the compound of above formula 3 may be tetrahydrochloride of formula 3-1 below.

[Formula 3-1]

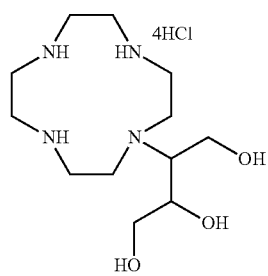

In addition, according to a specific embodiment of the present invention, the compound of above formula 2 may be a compound of formula 2-1 below, in which R is tert-butyl.

[Formula 2-1]

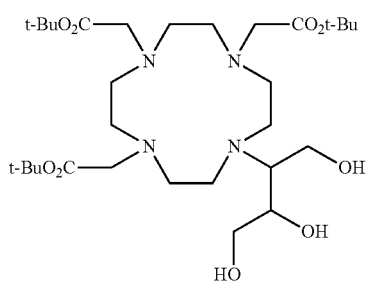

According to a specific embodiment of the present invention, the above step (S-1) may use water, $C_1$-$C_4$ alcohol, or a mixed solvent thereof. The mixed solvent used above may include preferably a mixed solvent of water and isopropyl alcohol, more preferably a mixed solvent containing water and isopropyl alcohol at a volume ratio (v/v) of 1:2 to 1:5, but is not limited thereto.

In the present specification, the term "alcohol" may refer to a compound in which a hydroxy group is bonded to a carbon atom of alkyl or substituted alkyl group.

According to a specific embodiment of the present invention, the above step (S-1) may perform the reaction in the presence of an inorganic base. Preferably, the inorganic base used above may include potassium carbonate ($K_2CO_3$), sodium hydrogen carbonate ($NaHCO_3$), potassium hydrogen carbonate ($KHCO_3$), or a mixture thereof, but is not limited thereto.

According to a specific embodiment of the present invention, the reaction of the above step (S-1) may be carried out at 70 to 90° C., preferably at 75 to 85° C., and more preferably 77 to 83° C., but is not limited thereto.

According to a specific embodiment of the present invention, the above step (S-1) may further include a process of crystallizing the compound of said formula 2.

The solvent used in the crystallization process may include methylene chloride, $C_3$-$C_{12}$ ester, or a mixture thereof. The mixture used above may include preferably a mixture of methylene chloride and ethyl acetate, more preferably a mixture of methylene chloride and ethyl acetate at a volume ratio (v/v) of 1:7 to 1:10, but is not limited thereto.

In the present specification, the term "crystallization" may refer to a process in which a solute dissolved in a solution is precipitated in a solid phase as a field of separation technology, so that a desired material may be easily separated through a crystallization process.

In the present invention, the compound of said formula 2 may be obtained at a high yield of 90% or more, preferably 95% or more through the above step (S-1).

Step (S-2): Synthesis of Gadobutrol (In-Situ)

In the preparation method of the present invention, the above step (S-2) may be a step in which a compound of formula 2 below is subjected to a basic hydrolysis reaction so as to prepare butrol, after which a gadolinium complex is formed in-situ without separate purification, so as to prepare a compound of formula 1 below.

[Formula 1]

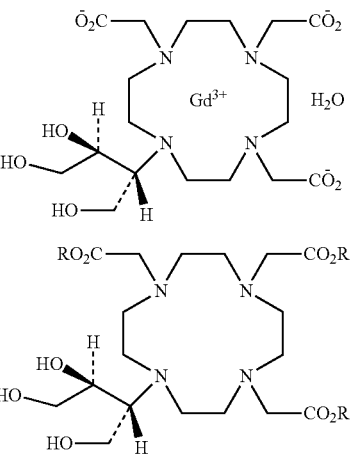

[Formula 2]

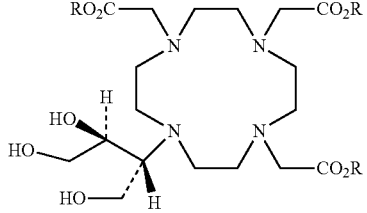

R is as defined above.

According to a specific embodiment of the present invention, the above step (S-2) may not use resin. As will be described later, the step (S-2) may have an advantage in that the salt generated during the reaction is effectively removed even without using resin, so that butrol may be prepared in a simpler process.

According to a specific embodiment of the present invention, the basic hydrolysis reaction may be performed by using conditions for a conventional basic hydrolysis reaction of ester. Preferably, the basic hydrolysis reaction may be performed by adding an aqueous sodium hydroxide solution or an aqueous potassium hydroxide solution to the compound of said formula 2.

In addition, the basic hydrolysis reaction may be performed at 60 to 100° C., preferably at 70 to 90° C., and more preferably 75 to 85° C., but is not limited thereto.

According to a specific embodiment of the present invention, after completion of the basic hydrolysis reaction, a butrol compound may be prepared by adjusting pH to an acidic condition, preferably by adjusting the pH with HBr. The pH may be adjusted to preferably 2 to 5, more preferably 3 to 4, and even more preferably 3.3 to 3.7. In the conventional method for synthesizing gadobutrol, the prepared butrol was to be purified with resin, etc. However, in the preparation method of the present invention, butrol may be used as it is in the reaction for forming a gadolinium complex in-situ without purification of butrol only by adjusting the pH.

According to a specific embodiment of the present invention, in the above step (S-2), a gadolinium ion source may be reacted with the butrol prepared through a basic hydrolysis reaction, so as to continuously prepare gadobutrol, which is a gadolinium complex of butrol.

According to a specific embodiment of the present invention, the gadolinium ion source used may include any compounds capable of supplying gadolinium ions, such as gadolinium oxide, gadolinium acetate, or gadolinium chloride, preferably gadolinium oxide, but is not limited thereto.

In the present invention, the reaction for forming the gadolinium complex may be carried out at 50 to 100° C., preferably at 70 to 95° C., and more preferably 87 to 93° C., but is not limited thereto.

According to a specific embodiment of the present invention, the above step (S-2) may include a salt removal process. The salt removal process may be performed through a nano filter. The nano filter used in the salt removal process may include, for example, DK1812 G/E (manufactured by Pure Tech P&T). The salt removal process may be simplified by removing salt remaining after the reaction without an additional process, may produce gadobutrol with a uniform quality such as a size thereof, and may increase the purity of gadobutrol. In addition, the salt removal process may be performed without using an organic solvent, an inorganic solvent or the like, and thus may be environmentally friendly with an economically beneficial effect. The salt removal process may be performed while an electrical conductivity of the filtrate is 500 μS/cm or less. If the electrical conductivity exceeds 500 μS/cm, the salt may not be sufficiently removed and thus the purity of gadobutrol may be lowered.

In addition, according to a specific embodiment of the present invention, the salt removal process may be performed by using 200 to 300 mL of water per 1 g of crude gadobutrol prepared by the reaction for forming the gadolinium complex, preferably by using 220 to 280 times of water, and more preferably 240 to 260 times of water, but is not limited thereto.

According to a specific embodiment of the present invention, the above step (S-2) may further include a gadobutrol crystallization process. The solvent used in the crystallization step may include water, $C_1$-$C_4$ alcohol, or a mixture thereof, preferably methanol or anhydrous ethanol, but is not limited thereto.

Step (S-3): Purification of Gadobutrol or Hydrates Thereof

The preparation method of the present invention may optionally further include a step (S-3) of purifying the crude gadobutrol prepared in the above step (S-2).

According to a specific embodiment of the present invention, the above step (S-3) may purify gadobutrol by using resin. The resin may include cation exchange resin and anion exchange resin, and preferably a volume ratio (v/v) thereof may be 1:1 to 1:3, but is not limited thereto.

According to another specific embodiment of the present invention, the above step (S-3) may further include a gadobutrol crystallization process. The solvent used in the crystallization step may include water, $C_1$-$C_4$ alcohol, or a mixture thereof, preferably ethanol, but is not limited thereto.

In the present invention, gadobutrol or hydrates thereof may be obtained from the above step (S-3) with high purity of 99% or more, preferably 99.5% or more, and more preferably 99.9% or more.

In the present invention, the compound represented by said formulas 1 to 3 may include the compound or salts thereof as well as solvates, hydrates and stereoisomers prepared therefrom, which are all included within the scope of the present invention.

According to a preferred specific embodiment of the present invention, gadobutrol may be prepared by a method represented by reaction formulas 1 to 2 below.

[Reaction Formula 1]

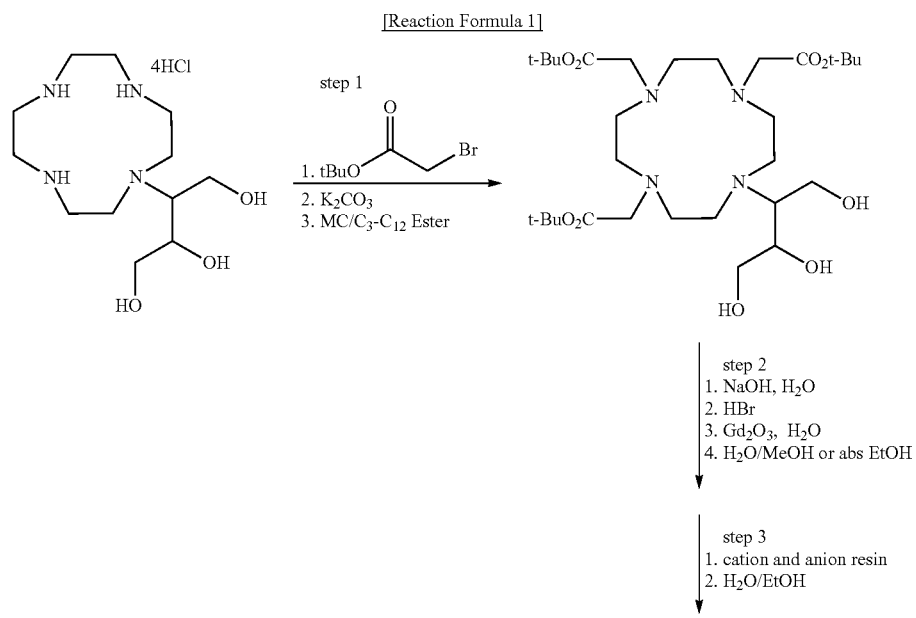

-continued

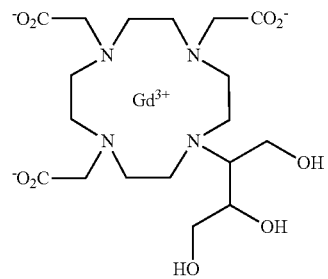

[Reaction Formula 2]

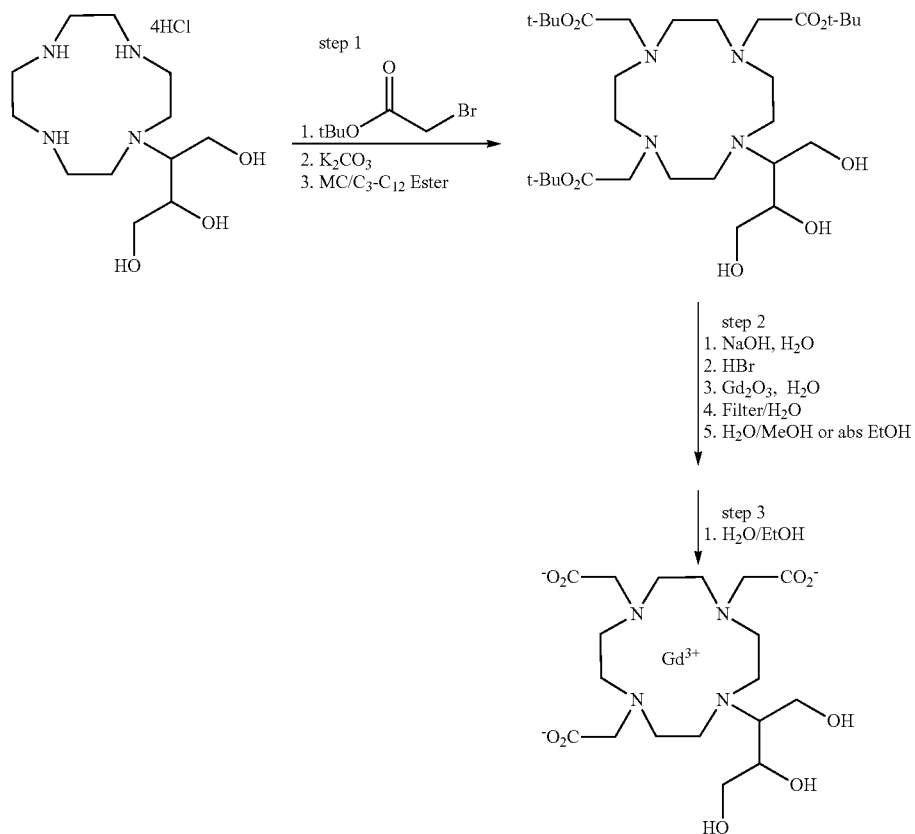

Advantageous Effects

The preparation method of the present invention can have an advantage of simplifying a process by forming a gadolinium complex in-situ without purification of a butrol intermediate and omitting a resin purification process unlike a conventional method for synthesizing gadobutrol. In addition, the preparation method of the present invention can be used to produce high-purity gadobutrol or hydrates thereof at a high yield only through the simple process as above, and thus can be useful in mass production.

BEST MODE FOR INVENTION

Hereinafter, the present invention will be described in detail through preferred embodiments for better understanding of the present invention. However, the following embodiments are provided only for the purpose of illustrating the present invention, and thus the present invention is not limited thereto.

In addition, the reagents and solvents mentioned below were purchased from Sigma-Aldrich Korea and Daejung Chemicals & Metals Co., Ltd., unless otherwise specified. IR was measured by using Cary 630 FTIR of Agilent Technologies, and HPLC was measured by using 1200 Series of Agilent Technologies, and Dionex Ultimate 3000 series and Dionex Corona Veo RS detector from Thermo scientific. $^{13}C$ NMR was measured at 100 MHz by using Brucker's Biospin AG, Magnet system 400'54 Ascend, and MS was measured by using 6120 Quadrupoe LC/MS of Agilent Technologies. Purity was measured by using an area % of HPLC and an analysis method of related substances of "Gadobutrol monohydrate" in the European Pharmacopoeia. With regard to elementary analysis, C, H and N were measured by using Flash EA-2000 Organic Elemental Analyzer of Thermo Scientific, and O was measured by using Flash EA-1112 Series Elemental Analyzer of Thermo Finnigan.

Example 1: Preparation of Gadolinium Complex (Gadobutrol) of 10-(2,3-dihydroxy-1(hydroxymethyl)propyl)-1,4,7,10-tetraazacyclododecane-1,4,7-triacetic acid Step 1: Preparation of tert-butyl-2,2',2"-(10-(1,3,4-trihydroxybutan-2-yl)-1,4,7,10-tetraazacyclododecane-1,4,7-triyl)triacetate A 3-(1,4,7,10-tetraazacyclododecan-1-yl)butane-1,2,4-triol 4 hydrochloride (100 g, 0.2368 mol) was dissolved in 500 ml of purified water and 1000 ml of isopropyl alcohol while being stirred. Potassium carbonate (327 g, 2.3684 mol) was added at room temperature, and tert-butylbromoacetate (143.2 g, 0.7434 mmol) was slowly added. At the end of the addition, a reaction was performed at 77 to 83° C., and at the end of the reaction, 200 ml of purified water was added and dissolved while being stirred. After dissolution, an organic layer was removed through concentration under reduced pressure, and the organic layer was separated by using 1000 ml of purified water and 1000 ml of toluene, and 500 ml of hydrochloric acid was added to the separated organic layer so as to separate a water layer. 500 ml of methylene chloride was added to the separated water layer, and pH was adjusted to 9.3 to 9.8 with sodium carbonate (100 g), and the organic layer was separated. The separated organic layer was dehydrated and then concentrated under reduced pressure. The concentrated residue was subjected to crystallization by using methylene chloride (200 ml) and ethyl acetate (1400 ml), and the resulting solid was filtered and dried to obtain 139.2 g (yield: 95%, purity: 97.7%) of the title compound.

Mass spectrum: m/e 619 [(M+H)+]
$^{13}$C-NMR (CDCl$_3$, 100 MHz): δ (ppm) 27.86, 28.16, 45.01, 45.20, 55.43, 55.82, 56.26, 59.62, 64.70, 70.66, 81.88, 82.12, 172.09,
Infrared spectrum (KBr, cm$^{-1}$): 3820, 2817, 1729, 1365, 1221, 1108, 1159.

Step 2: Preparation of Gadolinium Complex (Gadobutrol) of 10-(2,3-dihydroxy-1(hydroxymethyl)propyl)-1,4,7,10-tetraazacyclododecane-1,4,7-triacetic acid Tert-butyl-2,2',2"-(10-(1,3,4-trihydroxybutan-2-yl)-1,4,7,10-tetraazacyclododecane-1,4,7-triyl)triacetate (139.2 g, 0.225 mol) prepared in step 1 was dissolved in 557 ml of purified water while being stirred, and sodium hydroxide (31.5 g, 0.7875 mol) was added, after which an internal temperature was raised to 75 to 80° C. At the end of raising the temperature, a reaction was performed at the same temperature for three hours. After confirming the completion of the reaction, the resulting mixture was cooled to 15° C. or less.

After the end of cooling, pH was adjusted to 3.3 to 3.7 by using bromic acid, and gadolinium oxide (57.09 g, 0.1575 mol) was added after decolorization treatment. An internal temperature was raised to 87 to 93° C. and the resulting mixture was stirred at the same temperature for one hour. After confirming the completion of the reaction, the reaction solution was filtered by using diatomaceous earth. The filtrate was concentrated under reduced pressure. 139.2 ml of purified water was added to the concentrated residue, and the internal temperature was raised to 70° C. or higher, and dissolved while being stirred. After the end of the dissolution, 2785 ml of methanol was added and stirred under reflux for three hours. After cooling to room temperature, the resulting mixture was stirred at the same temperature for two hours or more, and filtered under a nitrogen atmosphere. The filtered crystals were dried under vacuum at the internal temperature of 50° C. or less so as to obtain 126.2 g of the title compound (yield: 90%, content: 83.0%).

Mass spectrum: m/e 606 [(M+H)+]
Infrared spectrum (KBr, cm$^{-1}$): 3295, 1639, 1592, 1384, 1327, 1269, 1079, 1016, 936, 721.

Example 2: Preparation of Gadolinium Complex (Gadobutrol) of 10-(2,3-dihydroxy-1(hydroxymethyl)propyl)-1,4,7,10-tetraazacyclododecane-1,4,7-triacetic acid Tert-butyl-2,2',2"-(10-(1,3,4-trihydroxybutan-2-yl)-1,4,7,10-tetraazacyclododecane-1,4,7-triyl)triacetate (139.2 g, 0.225 mol) prepared in step 1 of Example 1 was dissolved in 557 ml of purified water while being stirred, and sodium hydroxide (31.5 g, 0.7875 mol) was added, and an internal temperature was raised to 75 to 80° C. If heating was completed, a reaction was performed at the same temperature for three hours. After confirming the completion of the reaction, the reaction mixture was cooled to 15° C. or less.

After cooling was completed, pH was adjusted to 3.3 to 3.7 by using bromic acid, and gadolinium oxide (57.09 g, 0.1575 mol) was added after decolorization treatment. An internal temperature was raised to 87 to 93° C., and stirred at the same temperature for one hour. After confirming the completion of the reaction, the reaction mixture was cooled to room temperature and filtered by using diatomaceous earth. The filtrate was diluted, and salt was removed with a nano filter (DK1812 G/E (manufactured by Pure Tech P&T)) by using 34800 ml of water. The remaining mixed solution was concentrated under reduced pressure. The 139.2 ml of purified water was added to the concentrated residue, and the internal temperature was raised to 70° C. or higher, and the resulting mixture was dissolved while being stirred. After completion of the dissolution, 1392 ml of methanol was added and stirred under reflux for three hours. The resulting mixture was cooled to room temperature, stirred at the same temperature for two hours or more, and filtered under a nitrogen atmosphere. The filtered crystals were dried under vacuum at the internal temperature of 50° C. or less so as to obtain 82.7 g of the title compound (yield: 59%, purity: 99.97%).

Mass spectrum: m/e 606 [(M+H)+]
Infrared spectrum (KBr, cm$^{-1}$): 3403, 3269, 2856, 1595, 1375, 1318, 1273, 1087, 1005, 992, 932

Example 3: Preparation of Gadolinium Complex (Gadobutrol Monohydrate) of 10-(2,3-dihydroxy-1 (hydroxymethyl)propyl)-1,4,7,10-tetraazacyclododecane-1,4,7-triacetic acid A gadolinium complex of 10-(2,3-dihydroxy-1(hydroxymethyl)propyl)-1,4,7,10-tetraazacyclododecane-1,4,7-triacetic acid (126.2 g, 0.2025 mol) prepared in step 2 of Example 1 was dissolved in 1262 ml of purified water while being stirred. Resin containing 126 ml of cation exchange resin and 252 ml of anion exchange resin was added to the filtrate of gadolinium oxide, stirred, filtered, and concentrated under reduced pressure. The 126.2 ml of purified water was added to the concentrated residue, and the resulting mixture was stirred at an internal temperature of 70° C. or higher. After completion of the dissolution, 1262 ml of ethanol was added, and stirred under reflux for three hours. The resulting mixture was cooled to room temperature, stirred at the same temperature for two hours, and filtered under a nitrogen atmosphere. The filtered crystals were dried under vacuum at the internal temperature of 50° C. or lower so as to obtain 94.6 g of the title compound (yield: 75.0%, purity: 99.99%).

Mass spectrum: m/e 606 [(M+H)+]
Elemental Analysis for $C_8H_{31}N_4O_9Gd$, $H_2O$: C, 34.6 (34.7), H, 5.3 (5.3), N, 8.8 (9.0), O, 21.1 (25.7)
Infrared spectrum (KBr, cm$^{-1}$): 3403, 3269, 2856, 1595, 1318, 1273, 1087, 1005, 992, 932

Example 4: Preparation of Gadolinium Complex (Gadobutrol) of 10-(2,3-dihydroxy-1(hydroxymethyl)propyl)-1,4,7,10-tetraazacyclododecane-1,4,7-triacetic acid After completion of the dissolution, 79.9 g of the title compound (yield: 57%, purity: 99.97%) was obtained in the same manner as in Example 2, except that 2785 ml of methanol was added.

Mass spectrum: m/e 606 [(M+H)+]
Infrared spectrum (KBr, cm$^{-1}$): 3403, 3269, 3141, 2857, 1597, 1375 1320, 1273, 1066, 992, 932

Example 5: Preparation of Gadolinium Complex (Gadobutrol Monohydrate) of 10-(2,3-dihydroxy-1 (hydroxymethyl)propyl)-1,4,7,10-tetraazacyclododecane-1,4,7-triacetic acid After completion of the dissolution, 88.3 g of the title compound (yield: 63%, purity: 99.97%) was obtained in the same manner as in Example 2, except that 2785 ml of anhydrous ethanol was added instead of methanol.

Mass spectrum: m/e 606 [(M+H)+]
Elemental Analysis for $C_{18}H_{31}N_4O_9Gd$, $H_2O$: C, 34.6 (34.7), H, 5.3 (5.3), N, 8.8 (9.0), O, 21.1 (25.7)
Infrared spectrum (KBr, cm$^{-1}$): 3403, 3269, 3141, 2857, 1597, 1375, 1320, 1273, 1066, 992, 932

Comparative Example 1

Gadobutrol was prepared according to Scheme 1 disclosed to related art (Inorg. Chem. 1997, 36, 6086-6093).
Yield 65%, purity 95.98%
Infrared spectrum (KBr, cm$^{-1}$): Same as Example 1.

Comparative Example 2

Gadobutrol was prepared according to Scheme 2 disclosed to related art (Inorg. Chem. 1997, 36, 6086-6093).
Yield 63%, purity 93.57%
Infrared spectrum (KBr, cm$^{-1}$): Same as Example 1.

INDUSTRIAL APPLICABILITY

The preparation method of the present invention can have an advantage of simplifying a process by forming a gadolinium complex in-situ without purification of a butrol intermediate and omitting a resin purification process unlike a conventional method for synthesizing gadobutrol. In addition, the preparation method of the present invention can be used to produce high-purity gadobutrol or hydrates thereof at a high yield only through the simple process as above, and thus can be useful in mass production as well as related industry field.

The invention claimed is:
1. A method for preparing gadobutrol or hydrates thereof, the method comprising:
(S-1) subjecting a compound of formula 3 below or a salt thereof to a carboxymethylation reaction to prepare a compound of formula 2 below; and
(S-2) subjecting the compound of said formula 2 to a basic hydrolysis and forming a gadolinium complex in-situ to prepare a compound of formula 1 below:

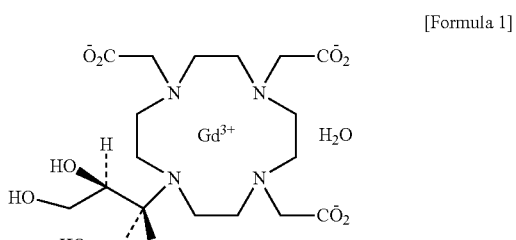

[Formula 1]

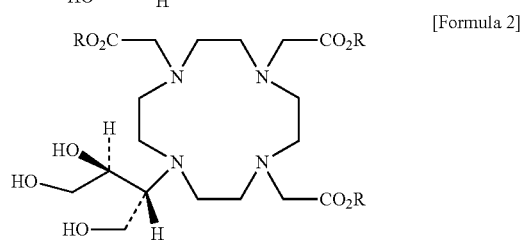

[Formula 2]

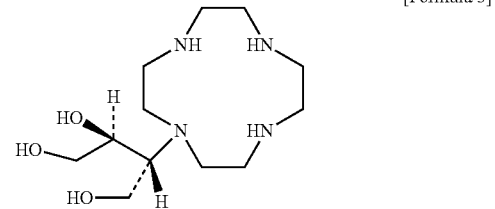

[Formula 3]

wherein, in above formula 2,
R is $C_1$-$C_4$ linear or branched-chain alkyl,
wherein said (S-1) is performed in a mixed solvent, wherein the mixed solvent is a mixture of water and isopropyl alcohol.
2. The method according to claim 1, wherein, in said (S-1), the compound of said formula 3 or the salt thereof and a compound of formula 4 below are reacted in the presence of a base:

[Formula 4]

wherein,
R is $C_1$-$C_4$ straight or branched-chain alkyl, and
X is halogen, TsO$^-$ or MsO$^-$.
3. The method according to claim 1, wherein the salt of the compound of said formula 3 in said (S-1) is 4 hydrochloride salt of formula 3-1 below:

[Formula 3-1]

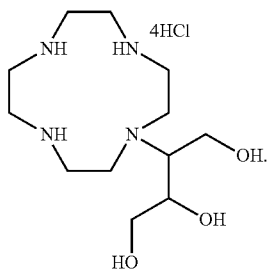

4. The method according to claim 1, wherein the compound of said formula 2 in said (S-1) is a compound of formula 2-1 below:

[Formula 2-1]

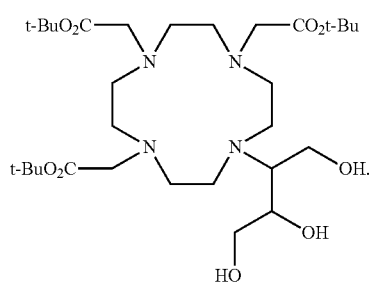

5. The method according to claim 2, wherein the base is an inorganic base.

6. The method according to claim 5, wherein the inorganic base is potassium carbonate ($K_2CO_3$), sodium hydrogen carbonate ($NaHCO_3$), potassium hydrogen carbonate ($KHCO_3$), or a mixture thereof.

7. The method according to claim 1, wherein said (S-1) further comprises a crystallization process.

8. The method according to claim 7, wherein a solvent used in the crystallization is methylene chloride, $C_3$-$C_{12}$ ester, or a mixture thereof.

9. The method according to claim 8, wherein the mixture is a mixture of methylene chloride and ethyl acetate.

10. The method according to claim 1, wherein said (S-2) does not use a resin.

11. The method according to claim 1, wherein said (S-2) comprises a process of adjusting pH to acid after completion of a basic hydrolysis reaction.

12. The method according to claim 11, wherein the pH is 2 to 5.

13. The method according to claim 1, wherein said (S-2) is to add a gadolinium ion source.

14. The method according to claim 13, wherein the gadolinium ion source is gadolinium oxide, gadolinium acetate, or gadolinium chloride.

15. The method according to claim 1, wherein said (S-2) comprises a salt removal process.

16. The method according to claim 15, wherein the salt removal process is performed through a nano filter.

17. The method according to claim 15, wherein an electrical conductivity of filtrate is 500 μS/cm or less in the salt removal process.

18. The method according to claim 15, wherein the salt removal process is performed by using 200 to 300 mL of water per 1 g of crude gadobutrol prepared by a reaction for forming the gadolinium complex.

19. The method according to claim 1, wherein said (S-2) further comprises a crystallization process.

20. The method according to claim 19, wherein a solvent used in the crystallization is water, $C_1$-$C_4$ alcohol, or a mixed solvent thereof.

21. The method according to claim 20, wherein the solvent used in the crystallization is methanol or anhydrous ethanol.

22. The method according to claim 1, wherein said method further comprises (S-3) purifying crude gadobutrol with resin.

23. The method according to claim 22, wherein the resin comprises a cation exchange resin and an anion exchange resin.

24. The method according to claim 23, wherein a volume ratio of the cation exchange resin and the anion exchange resin is 1:1 to 1:3.

25. The method according to claim 1, wherein said (S-3) further comprises a crystallization process.

26. The method according to claim 25, wherein a solvent used in the crystallization is water, $C_1$-$C_4$ alcohol, or a mixed solvent thereof.

27. The method according to claim 26, wherein a solvent used in the crystallization is ethanol.

28. A method for preparing gadobutrol or hydrates thereof, the method comprising:
(S-1) subjecting a compound of formula 3 below or a salt thereof to a carboxymethylation reaction to prepare a compound of formula 2 below; and
(S-2) subjecting the compound of said formula 2 to a basic hydrolysis and forming a gadolinium complex in-situ to prepare a compound of formula 1 below:

[Formula 1]

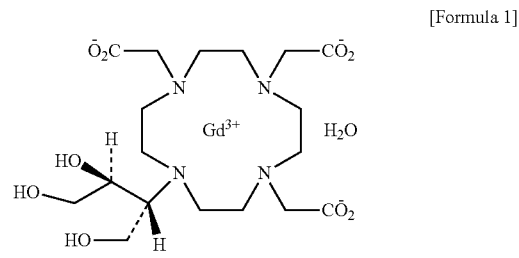

[Formula 2]

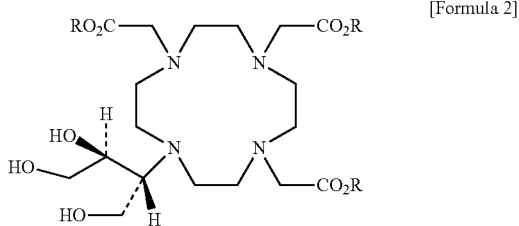

[Formula 3]

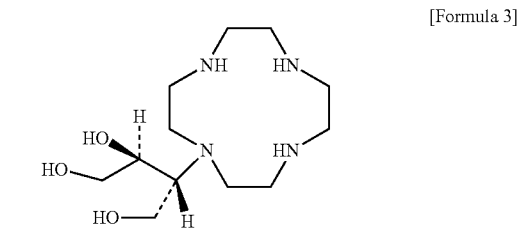

wherein, in above formula 2,
R is $C_1$-$C_4$ linear or branched-chain alkyl,
wherein said (S-2) does not use a resin.

29. The method according to claim 28, wherein said (S-2) comprises a salt removal process.

30. The method according to claim 29, wherein the salt removal process is performed through a nano filter.

* * * * *